United States Patent [19]
Gorlin et al.

[11] Patent Number: 5,833,956
[45] Date of Patent: Nov. 10, 1998

[54] ORAL COMPOSITION CONTAINING AN ANIONIC, A NONIONIC AND AN AMPHOTERIC SURFACTANT SYSTEM

[75] Inventors: Philip Anthony Gorlin, Monmouth Junction; Clarence Robbins, Martinsville; John Curtis, Bloomsbury; Richard Crawford, Asbury; Ammanuel Mehreteab, Piscataway; Jiashi Tarng, Dayton, all of N.J.

[73] Assignee: Colgate-Palmolive Company, New York, N.Y.

[21] Appl. No.: 825,807

[22] Filed: Apr. 2, 1997

[51] Int. Cl.$^6$ ....................................... A61K 7/16
[52] U.S. Cl. .............................................. 424/49
[58] Field of Search ................................. 424/49

[56] References Cited

U.S. PATENT DOCUMENTS

| | | | |
|---|---|---|---|
| 4,920,100 | 4/1990 | Lehmann et al. | 424/49 |
| 5,190,747 | 3/1993 | Sekiguchi et al. | 424/56 |
| 5,292,502 | 3/1994 | Burke et al. | 424/54 |
| 5,628,985 | 5/1997 | Stiller et al. | 424/49 |
| 5,630,999 | 5/1997 | Burke et al. | 424/49 |
| 5,639,733 | 6/1997 | Koike et al. | 514/25 |

*Primary Examiner*—Peter F. Kulkosky
*Attorney, Agent, or Firm*—Henry S. Goldfine

[57] ABSTRACT

The invention provides a substantially nonirritating oral composition containing a surfactant system comprised of a combination of an anionic surfactant, an amphoteric surfactant and a nonesterified alkyl polyglucoside surfactant.

8 Claims, No Drawings

ORAL COMPOSITION CONTAINING AN ANIONIC, A NONIONIC AND AN AMPHOTERIC SURFACTANT SYSTEM

BACKGROUND OF THE INVENTION

1. Field of the Invention

The present invention relates to a nonirritating oral composition, and specifically to a substantially nonirritating oral composition exhibiting high foam properties.

2. The Prior Art

Sodium lauryl sulfate (SLS) is a widely used surfactant in oral compositions, including dentifrices. Surfactants, and particularly anionic surfactants, such as SLS, serve as a solubilizing, dispersing, emulsifying and wetting agent for the other ingredients present in the dentifrice and are especially effective in solubilizing the flavor present. A cosmetic effect of the surfactant is that it promotes foaming of the oral composition. Oral compositions with strong foaming ability are preferred by consumers since the foaming provides the perception that the oral composition cleans effectively only if it foams well.

The incorporation of anionic surfactants such as SLS in oral compositions such as dentifrices is known to cause adverse reactions to oral tissue. One example of such an adverse reaction related to SLS is gingival irritation.

U.S. Pat. No. 5,190,747 discloses the use of certain nonionic surfactants in combination with one or more of the water-soluble anionic salts of alkyl sulfates, N-acylamino acids or N-acylmethyl taurines, including therein sodium lauryl sulfate; which have positive taste and foam characteristics for use in oral compositions, such as dentifrices. The nonionic surfactants of U.S. Pat. No. 5,190,747 are limited to fatty acid esters of a hexose or an alkyl glycoside; in support thereof an example of a nonesterified $C_{10}$ alkyl polyglycoside surfactant is stated to have a keen bitter or oily taste and to provide limited foaming activity.

U.S. Pat. No. 5,292,502 discloses a substantially nonirritating oral composition containing a purified form of sodium lauryl sulfoacetate surfactant having admixed therewith less than 18% non-dodecyl sodium sulfoacetate impurities. U.S. Pat. No. 5,292,502 further discloses that the inclusion of a nonionic or an amphoteric surfactant serves to increase the foaming ability of the oral composition to consumer desirable levels and can further reduce the irritability of the purified sodium lauryl sulfoacetate. The nonionic compositions disclosed included ethylene oxide containing polymers and oxygen containing heterocylic nitrogen compounds. The amphoteric compounds include amidobetaine compounds such as cocoamidoethyl betaine, cocoamidopropyl betaine, lauramidopropyl betaine and the like.

Accordingly, there is a continuing need for nonirritating oral compositions which may exhibit further mildness benefits and can utilize alternative raw materials.

SUMMARY OF THE INVENTION

In accordance with the present invention, there is provided an oral composition exhibiting substantially reduced gingival irritancy when applied to the oral cavity and which has an acceptable taste; wherein the composition contains as a surfactant system, a combination of an anionic surfactant, an amphoteric surfactant and a nonesterified alkyl polyglucoside surfactant.

As will hereinafter be demonstrated, anionic surfactants such as SLS, when present in an oral composition in combination with both an amphoteric surfactant and a nonesterified alkyl polyglucoside surfactant unexpectedly provide a composition which is substantially nonirritating to gingival tissue without sacrificing any foaming properties.

DETAILED DESCRIPTION OF THE PREFERRED EMBODIMENTS

The term "oral composition" is used herein to designate products which, in the ordinary course of usage, are retained in the oral cavity for a time sufficient to contact substantially all of the dental surfaces but are not intentionally ingested. Such products include, for example, dentifrices, gels, mouthwashes, chewing gums and lozenges.

Dentifrices may be substantially solid or pasty in character, such as toothpaste, gel or dental cream. The vehicle of such solid or pasty oral preparations generally contains a polishing material, and includes a water-phase with humectant which is preferably glycerin or sorbitol or an alkylene glycol such as polyethylene glycol or propylene glycol, wherein the water is present typically in amount of about 3 to 50% by weight, more typically about 5 to 20% by weight, and the glycerin, sorbitol and or/alkylene glycol ingredients total about 15 to about 70% by weight of the dentifrice, more typically about 25 to about 50% by weight.

The oral compositions of the present invention also include products which are substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

Anionic surfactants suitable for use in the surfactant system of the present invention include water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, alkyl ethoxy sulfates, monoalkylphosphates, α-olefin sulphonates, higher fatty acid esters of 1,2-dihydroxypropane sulfonate, organic phosphates esters, such as mono- and di-alkylethoxyphosphates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. A preferred anionic surfactant is sodium lauryl sulfate.

Amphoteric surfactants suitable for use in the surfactant system of the present invention include betaine compounds having the formula:

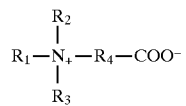

wherein R is an alkyl group having 10 to about 20 carbon atoms, preferably 12 to 16 carbon atoms or the amido radical:

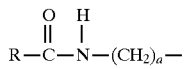

wherein R is an alkyl group having about 10 to 20 carbon atoms and a is the integer 1 to 3; $R_2$ and $R_3$ are each alkyl groups having 1 to 3 carbons and preferably 1 carbon and $R_4$ is an alkylene or hydroxyalkylene group having from 1 to 4 carbon atoms and optionally, 1 hydroxyl group. Typical alkyl dimethyl betaines include decyl betaine or 2-(N-decyl-N,N-dimethylammonio) acetate, myristyl betaine, palmityl betaine, lauryl betaine, cetyl betaine, stearyl betaine, and the like. The amidobetaines similarly include cocoamidoethyl betaine, cocoamidopropyl betaine, lauramidopropyl betaine and the like. A preferred betaine is cocoamidopropyl betaine, which is available from Goldschmidt Chemical Corporation, Hopewell, Va., under the trademark of Tegobetaine.

Nonesterified alkyl polyglucosides suitable for use in the surfactant system of the present invention are formed by combining fatty alcohols with a carbohydrate (monosaccharide) in the presence of an acid catalyst (Fischer Glycosidation process). The nonesterified nonionic alkyl polyglucosides (hereinafter referred to as APG) useful in the present invention are those having 6 to 16 carbons in the alkyl group, preferably 8 to 16 carbons in the alkyl group, and having a glucoside hydrophilic group containing from about 1 to about 3 glucoside units (i.e. saccharide structures), preferably from about 1.2 to about 3 and most preferably from about 1.3 to 2.7 glucoside units, such as 1.3, 1.4, 1.5, 1.6, 2.0, or 2.6 glucoside units. Of course, the number of glucoside units in any particular surfactant molecule will be a whole number (i.e. an integer); however, for any actual physical sample of alkyl glucoside surfactants there will, in general, be a range of glucoside units, and it is the average value that characterizes a particular surfactant product. The alkyl glucosides with lower D.P. (degree of polymerization, or average ratio of saccharide structures to alkyl groups), the lower the average saccharide or hydrophile content in the surfactant, tend to provide more copious foaming. Whereas, alkyl glucosides with higher DP, higher average saccharide or hydrophile content in the surfactant, tend to be more soluble for the same alkyl chain length.

A suitable alkyl polyglucoside identified by the Cosmetic, Toiletry, and Fragrance Association (the CTFA) as decyl glycoside and having the general empirical formula of $C_{16}H_{32}O_6$ is a product obtained from the condensation of decyl alcohol with a glucose polymer. Decyl glycoside is sold under the Plantaren 2000 trademark by Henkel Corporation, Cospha (Cosmetics-Pharmaceutical) Division, Hoboken, N.J. Plantaren 2000 has an average DP of 1.4 and an alkyl chain length distribution of from $C_8$ to $C_{16}$. A second suitable alkyl polyglucoside identified by the CTFA is lauryl glucoside, a product obtained from the condensation of lauryl alcohol with a glucose polymer, having an average DP of 1.4 and an alkyl chain length distribution of from $C_{12}$ to $C_{16}$. See, Siracusa, *Alkyl Polyglycosides: A New Category of Surfactants,* HAPPI—Household & Personal Products Industry Journal, Rodman Publishing Corp., Ramsey, N.J., p. 100–108 (April 1992), incorporated herein by reference.

The total amount of surfactant comprising the surfactant system present in the composition ranges from about 0.5% to about 3.0% by weight, preferably about 1.5% to about 2.5% by weight. The amount of anionic surfactant ranges from about 0.2 to about 2.0% by weight, preferably from about 0.5 to about 2.0% by weight. The amount of amphoteric surfactant ranges from about 0.2 to about 1.0% by weight. The amount of nonesterified nonionic surfactant ranges from about 0.2 to about 2.0% by weight, preferably from about 0.5 to about 2.0% by weight. Hence, the combined anionic, amphoteric, nonesterified nonionic surfactant system of the subject invention contains relative quantities of anionic, amphoteric and nonesterified nonionic surfactant in the weight ratio of the total oral composition of from 0.2–2.0%:0.2–1.0%:0.2–2.0%, respectively, and preferably 0.5–2.0%:0.2–1.0%:0.5–2.0%, respectively.

Dentifrice compositions also typically contain polishing materials including crystalline silica, having a particle size of up to about 20 microns, such as a synthetic precipitated amorphous silica available under the tradename Zeodent 115, manufactured by J. M. Huber Chemicals Division, Havre de Grace, Md.; a hydrated silica available under the tradename Zeodent 165, from J. M. Huber; complex amorphous alkali metal aluminosilicates; as well as, sodium bicarbonate, calcium carbonate, calcium pyrophosphate, dicalcium phosphate and calcined alumina.

Dentifrices prepared in accordance with the present invention typically contain a natural or synthetic thickener or gelling agent in proportions of about 0.1 to about 5% by weight, preferably about 0.5 to about 2% by weight. Suitable thickeners include Irish moss; carrageenan; gum tragacanth; starch; polyvinylpyrrolidone; hydroxyethylpropyl cellulose; hydroxybutyl methyl cellulose; hydroxypropyl methylcellulose; hydroxyethyl cellulose; sodium carboxymethyl cellulose (NaCMC); and colloidal silica such as available from W. R. Grace and Co., Davison Chemical Division, Baltimore, Md. under the tradenames of Sylodent 15 or Syloid 244.

A preferred thickener is a carrageenan thickening gum available from FMC, Food Ingredients Division, Philadelphia, Pa., under the tradename Viscarin TP348. Carrageenan is a high molecular weight linear polysaccharide derived from sea plants, carrageenan makes up approximately 2 to 7% of the plant and is found between the cellulosic fibers. Carrageenan is composed of repeating galactose units; 3,6-anhydrogalactose (3,6-AG), both sulfated and unsulfated, joined by alternating 1-3,β 1-4 glycosidic linkages. Viscarin TP 348 is high in iota carrageenan content, containing approximately 96% iota, 4% lambda and no kappa carrageenan.

The oral composition may also contain a source of fluoride ions, or fluoride-providing compound, as an anti-caries agent, in an amount sufficient to supply about 25 ppm to 5,000 ppm of fluoride ion and preferably 500 to 1500 ppm fluoride ion. Among these compounds are inorganic fluoride salts, such as alkali metal salts, for example, sodium fluoride, potassium fluoride, sodium fluorosilicate, ammonium fluorosilicate and sodium monofluorphosphate.

Antibacterial agents may also be included in the oral compositions of the present invention. Especially useful are non-cationic antibacterial agents based on phenolic and bisphenolic compounds, halogenated diphenyl ether, benzoate esters and carbanilides. Examples of such compounds are 4-chlorophenol, 2,2'-trichloro-2-hydroxy-diphenyl ether (triclosan), esters of p-hydroxybenzoic acid, especially methyl, ethyl, butyl and benzyl esters, 3,4,4'-trichlorocarbanalide and 3,3',4-trichlorocarbanilide. Triclosan at concentrations ranging from 0.03% to 1% by weight is preferred for use in the compositions of the present invention.

Any suitable flavoring or sweetening material may also be employed. Examples of suitable flavoring constituents include flavoring oils, e.g. oil of spearmint, peppermint, wintergreen, clove, sage, eucalyptus, marjoram, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% more of the oral care composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetraalkali metal pyrophosphate salts such as di- and tetrasodium pyrophosphate and di- and tetrapotassium pyrophosphate. These agents, when present, are incorporated in the compositions of the present invention in amounts which do not substantially adversely affect the properties and characteristics desired.

The preparation of dentifrices is well-known in the art. U.S. Pat. Nos. 3,996,863, 3,980,767, 4,328,205, and 4,358,437, describe toothpastes and methods of production thereof, which may be utilized for production of the dentifrices according to the present invention. For instance, one method for making toothpaste compositions of the present invention involves forming a dispersion containing a gelling agent or thickener such as sodium carboxymethyl cellulose or Iota carrageenan and a preservative such as sodium benzoate, if employed, in a humectant such as glycerin. Water may also be present in the dispersion. Additional humectant and water may then be mixed with the dispersion and a homogeneous paste, gel or cream is formed. A polishing material such as crystalline silica, a surfactant, such as the surfactant system of the present invention and flavor are then added. The toothpaste is then thoroughly deaerated (e.g. in vacuo) and tubed. The formulation may be deaerated during, as well as, after mixing.

The following examples are further illustrative of the nature of the present invention, but it is understood that the invention is not limited thereto. All amounts and proportions referred to herein and in the appended claims are by weight, unless otherwise indicated.

EXAMPLE I

A dentifrice of the present invention designated Composition A was prepared following the above discussed procedure containing a surfactant system of 1.0% by weight of the anionic surfactant, sodium lauryl sulfate (SLS); 0.5% by weight of the amphoteric surfactant, cocoamidopropyl betaine (CAPB); and 1.0% by weight of the nonesterified nonionic surfactant, APG (as Plantaren 2000), the detailed formulation for which is shown in Table I. A series of comparative compositions were prepared, designated Compositions B, C, D, and E, these compositions differing from Composition A only in the relative presence/amounts of anionic, amphoteric and nonesterified nonionic APG surfactants within each composition, as shown in Table I, below.

The foaming ability of the Compositions A–E was assessed by subjecting each formulation to an inverted cylinder foam test method. The inverted cylinder foam test method comprises, first placing 100 milliliters (ml) of a 2.5% by weight aqueous solution of the dentifrice in a 500 ml graduated cylinder under ambient room conditions of temperature and pressure. The 500 ml graduated cylinder is then inverted 40 times and the resulting ml level of the foam is recorded within the 500 ml graduated cylinder. Using this test, a foam level of over about 100 ml is considered to be minimally consumer acceptable in an oral product. The results of subjecting the dentifrice Compositions A–E to this test method are presented in Table II, below.

TABLE I

| DENTIFRICE | COMPOSITION | | | | |
|---|---|---|---|---|---|
| | A | B | C | D | E |
| Surfactant System | | | | | |
| SLS | 1.0 | 2.5 | 2.0 | 1.5 | 1.5 |
| CAPB* | 0.5 | — | 0.5 | 1.0 | — |
| Plantaren 2000** | 1.0 | — | — | — | 1.0 |
| Other Ingredients | | | | | |
| PEG 600 | 3.0 | 3.0 | 3.0 | 3.0 | 3.0 |
| Viscarin TP389 | 0.3 | 0.3 | 0.3 | 0.3 | 0.3 |
| Sorbitol | 61.997 | 64.157 | 62.997 | 61.827 | 63.157 |
| Distilled Water | 9.26 | 7.1 | 8.26 | 9.43 | 6.0 |
| TiO$_2$ | 0.5 | 0.5 | 0.5 | 0.5 | 0.5 |
| Saccharin | 0.2 | 0.2 | 0.2 | 0.2 | 0.2 |
| Sodium Fluoride | 0.243 | 0.243 | 0.243 | 0.243 | 0.243 |
| Zeodent 115 | 18.0 | 18.0 | 18.0 | 18.0 | 18.0 |
| Zeodent 165 | 4.0 | 4.0 | 4.0 | 4.0 | 4.0 |
| TOTAL | 100.0 | 100.0 | 100.0 | 100.0 | 100.0 |

Notes:
*CAPB is a 31% aqueous solution.
**Plantaren is a 50% aqueous solution.

TABLE II

Dentifrice Composition Foaming Levels

| DENTIFRICE | COMPOSITION | | | | |
|---|---|---|---|---|---|
| | A | B | C | D | E |
| ml Level Reached by Foam | 268 | 113 | 213 | 225 | 306 |

The data recorded in Table II shows that all the dentifrice compositions exhibited higher foam levels than when SLS alone was the sole surfactant (Composition B).

EXAMPLE II

Anionic surfactants such as SLS are believed to cause gingival irritation because they penetrate the stratum corneum of the skin or the "barrier" (i.e. percutaneous absorption), and then react with the inner cells of the epidermis. In vivo, the percutaneous absorption has been found to be difficult to measure. An in vitro test used by the art involves a surfactant's ability to solubilize zein in water. Zein is a generally insoluble maize protein and the ability of a surfactant to solubilize it in water has been shown to correlate well with in vivo irritation results.

Specifically, in this "zein test," a 0.83% surfactant solution is mixed with 0.5 g zein for 1 hour at room temperature. After moderate centrifugation and vacuum filtration, the resulting solute is diluted 20 times in a 1% SLS solution. Excess BCA, bicinchoninic acid, from the Pierce Chemical Company of Rockford, Ill., is added to the diluted solute to provide $Cu^{2+}$, which is oxidized by the zein to form a $Cu^{+1}$ $(BCA)_2$ complex whose quantity is measurable via UV-visible light spectrophotometry at 562 nanometers (nm). See, P. K. Smith et al., "Measurement of Protein Using Bicinchoninic Acid", *Analytical Biochemistry* 150, 76–85 (1985). The quantity of zein present in the dilute solute (milligrams of zein per milliliter of solute) is established by comparing the UV-visible light 562 nm peak's integrated area against a series of standard peaks' integrated areas that were previously established with known quantities of zein. The lower the amount of zein dissolved in the surfactant solution, the milder a surfactant is with respect to gingival irritation. Conversely, the more zein dissolved in the surfactant solution, the more irritating is the surfactant.

A 0.83% aqueous solution of the surfactant system of dentifrice A (i.e. SLS, CAPB and nonesterified nonionic APG in a 1:0.5:1 proportion, respectively) was prepared. Following the zein testing procedure detailed above, a zein score (i.e. mg of zein per ml of solute) was determined and this result is recorded in Table III, below.

The zein testing of the surfactant system of Composition A was repeated for the surfactant systems of comparative Compositions B–E presented in Table I, above. The zein scores for comparative dentifrices B–E is recorded in Table III.

TABLE III

Zein Test of Surfactant Systems Used in Compositions A–E

| DENTIFRICE | COMPOSITION | | | | |
|---|---|---|---|---|---|
| | A | B | C | D | E |
| Zein Scores | 7.7 | 29.6 | 22.4 | 15.9 | 17.9 |

Composition A exhibited a Zein Score of 7.7 which was at least 50% to about 75% less than the Zein scores of the comparative compositions B–E, indicating the substantial and unexpected reduction in gingival irritation observed in the use of Composition A, as compared to Compositions B–E.

What is claimed is:

1. An oral composition comprising a surfactant system of 0.2 to 2.0% by weight anionic sodium lauryl sulfate surfactant, 0.2 to 1.0% by weight of an amidobetaine amphoteric surfactant as the only amphoteric surfactant being present and 0.2 to 2.0% by weight of a nonesterified alkyl polyglucoside surfactant, incorporated in an orally acceptable vehicle, the composition being substantially nonirritating to gingival tissue.

2. The composition of claim 1, wherein the amphoteric surfactant is cocoamidopropyl betaine and the nonesterified alkyl polyglucoside is lauryl polyglucose or decyl polyglucose having an alkyl chain length ranging from $C_8$ to $C_{16}$.

3. The composition of claim 1 wherein the oral composition is a paste dentifrice.

4. The composition of claim 1 wherein the anionic, nonionic, nonesterified nonionic surfactant system is from about 0.5 to 3% by weight of the total oral composition.

5. A method for promoting foaming of oral compositions comprising: preparing and administering to the oral cavity an oral composition having a surfactant system containing a mixture of 0.2–2.0% by weight of sodium lauryl sulfate, 0.2 to 1.0% by weight of an amidobetaine amphoteric surfactant as the only amphoteric surfactant being present, and 0.2 to 2.0% by weight of a nonesterified alkyl polyglucoside surfactant, incorporated in an orally acceptable vehicle, the composition being substantially nonirritating to gingival tissue.

6. The method of claim 5 wherein the amphoteric surfactant is cocoamidopropyl betaine and the nonesterified alkyl polyglucoside is lauryl polyglucose or decyl polyglucose having an alkyl chain length ranging from $C_8$ to $C_{16}$.

7. The method of claim 5 wherein the oral composition is a paste dentifrice.

8. The method of claim 5 wherein the anionic, nonionic, nonesterified nonionic surfactant system is from about 0.5 to 3% by weight of the total oral composition.

* * * * *